(12) United States Patent
Hu

(10) Patent No.: US 9,120,722 B1
(45) Date of Patent: Sep. 1, 2015

(54) OPTICALLY ACTIVE VALINE COMPLEX AND A METHOD FOR PRODUCING THE SAME

(71) Applicant: Songzhou Hu, Princeton, NJ (US)

(72) Inventor: Songzhou Hu, Princeton, NJ (US)

(73) Assignee: Wellman Biosciences Co. Ltd., Huanggang (CN)

( * ) Notice: Subject to any disclaimer, the term of this patent is extended or adjusted under 35 U.S.C. 154(b) by 0 days.

(21) Appl. No.: 14/121,223

(22) Filed: Aug. 14, 2014

(51) Int. Cl.
| C07C 227/40 | (2006.01) |
| C07C 233/83 | (2006.01) |
| C07C 229/08 | (2006.01) |
| C07C 231/12 | (2006.01) |
| C07C 227/34 | (2006.01) |

(52) U.S. Cl.
CPC ............. C07C 227/40 (2013.01); C07C 227/34 (2013.01); C07C 229/08 (2013.01); C07C 231/12 (2013.01); C07C 233/83 (2013.01)

(58) Field of Classification Search
CPC .............................. C07C 227/40; C07C 227/34
See application file for complete search history.

(56) References Cited

U.S. PATENT DOCUMENTS

| 3,182,079 A | 5/1965 | Tatsumi et al. |
| 4,519,955 A | 5/1985 | Chibata et al. |
| 4,610,827 A | 9/1986 | Yukawa et al. |
| 4,667,054 A | 5/1987 | Miyazawa et al. |
| 5,689,001 A | 11/1997 | Hasegawa |
| 6,072,083 A | 6/2000 | Hasegawa |

FOREIGN PATENT DOCUMENTS

| CN | 1477096 A | | 2/2004 |
| CN | 101659622 A | | 3/2010 |
| CN | 102796018 A | | 11/2012 |
| JP | 62114968 A | * | 5/1987 |
| JP | S 6296454 A | | 5/1987 |
| JP | 2006169158 A | | 6/2006 |

* cited by examiner

*Primary Examiner* — Sudhakar Katakam

(57) ABSTRACT

The present invention discloses an optically active complex of L-valine N-benzoyl-L-alanine, comprising one mole each of L-valine and N-benzoyl-L-alanine. N-benzoyl-L-alanine is found to react selectively with L-valine to form the novel crystalline complex even in the presence of D-valine, other amino acids, and impurities present in synthetic DL-valine and in the crude L-valine from the hydrolysis of protein and fermentation. The optically active L-valine N-benzoyl-L-alanine is used as an intermediate for the optical resolution of DL-valine and for the purification of L-valine.

10 Claims, No Drawings

OPTICALLY ACTIVE VALINE COMPLEX AND A METHOD FOR PRODUCING THE SAME

FIELD OF THE INVENTION

The present invention relates to an optically active complex of valine: N-benzoyl-alanine, represented by the general formula:

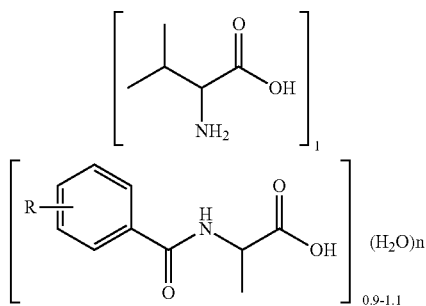

Wherein R is hydrogen, fluoro, chloro, bromo, methyl, ethyl, isopropyl, methoxy, nitro group in ortho, meta, and para positions, n is 0, ½, and 1 and a method for producing such complexes. In addition, the phenyl group can also be di- and tri-substituted with R groups.

The novel substances of the present invention are useful as intermediates for optical resolution of racemic DL-valine and for the purification of L-valine, which is generally obtained by hydrolysis of proteins or by fermentation of microorganisms having the ability to produce L-valine.

BACKGROUND OF THE INVENTION

Optically active valines are important starting materials for the production of pharmaceutical and agricultural products. L-valine is a key starting material for the production of valsartan, valganciclovir, ritonavir, and lopinavir, while D-valine is used in the production of valnemulin, a pleuromutilin antibiotic, and tau-fluvalinate, a synthetic pyrethroid. As one of the essential amino acids, L-valine also finds wide applications in human and animal nutrition.

Valine obtained by synthesis is a racemate (DL-form) and should be optically resolved. On the other hand, L-valine, obtained from hydrolysis of proteins or from fermentation of suitable microorganism, is often contaminated with other amino acids of similar chemical and physical properties, such as L-alanine, L-leucine, and L-isoleucine. The separation of L-valine from these contaminating amino acids remains a major challenge in the industry.

The conventional methods for resolving DL-valine include the following:

(1) Asymmetric hydrolysis of N-acetyl valine by acylase to yield L-valine and N-acetyl D-valine. Hydrolysis of N-acetyl D-valine with an acid yields D-valine.

(2) Direct resolution of DL-valine hydrochloride (U.S. Pat. No. 3,182,079 and No. 4,667,054) or DL-valine xylenesulfonate (JP 62096454A) by preferential crystallization to yield L-valine and D-valine.

(3) Resolution of DL-valine with optically active resolving agents such as N-acyl aspartic acid (U.S. Pat. No. 4,610,827), dibenzoyl-tartaric acid (CN 1477096A, CN101659622A), diacetyl-tartaric acid (CN 102796018B), 2-phenoxypropionic acid (JP 2006169158A), and phenylethanesulfonic acid (U.S. Pat. No. 4,519,955).

However, the enzymatic method mentioned in (1) is disadvantageous since it involves acetylation of DL-valine and requires the use of an expensive enzyme.

As for the resolution by preferential crystallization in (2), the process is difficult to control and problematic to scale up.

When the inventor of the present invention made a follow-up of the known processes using optically active resolving agents in (3), it is found that the processes are extremely disadvantageous for industrial practice. N-acyl-L-aspartic acid forms L-valine complex with poor selectivity and low yield. Even with repeated crystallization of the intermediate complex, the optical purity of L-valine remains unsatisfactory.

Dibenzoyl-L-tartaric acid and diacetyl-L-tartaric acid, while useful as resolving agents for DL-valine, are unstable under the working conditions and are partially hydrolyzed to tartaric acid, benzoic acid, and acetic acid. The recovery and recycling of these resolving agents are problematic, thus rendering the process economically disadvantageous.

Optically active 2-phenoxypropionic acid and 2-phenylethanesulfonci acid can only resolve DL-valine partially and in low optical purity. Moreover, these two resolving agents are expensive, commercially unavailable, and complicated to prepare.

To purify the crude L-valine to yield high purity L-valine, U.S. Pat. No. 5,689,001 and No. 6,072,083 disclose the use of p-isopropylbenzene sulfonic acid and p-ethylbenzene sulfonic acid, respectively, to form crystalline valine salts as intermediates. However, these two sulfonic acids are not selective and their salts with L-valine are quite soluble in water (7.8% and 14.5%, respectively). As a result, in the process of using these sulfonic acids, the recovery yield for L-valine is low and the purity of L-valine needs further improving for its use in the production of pharmaceuticals.

After devoted research for developing commercially advantageous methods for optical resolution of DL-valine and for the purification of L-valine, the present inventor has discovered that optically active N-benzoyl-L-alanine reacts selectively with L-valine to form a novel crystalline complex, L-valine N-benzoyl-L-alanine, comprised of 1 mole each of L-valine and N-benzoyl-L-alanine, even in the presence of D-valine, amino acids (e.g., alanine, leucine, isoleucine, serine, phenylalanine, tyrosine, methionine, aspartic acid, and glutamic acid), and other impurities found in synthetic DL-valine and in the crude L-valine from protein hydrolysate and fermentation. This finding has become the basis for the accomplishment of this invention.

DESCRIPTION OF THE INVENTION

The present invention relates to an optically active valine N-benzoyl-alanine complex comprising 1 mole of valine and 1 mole of N-benzoyl-alanine of the general formula:

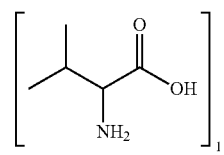

-continued

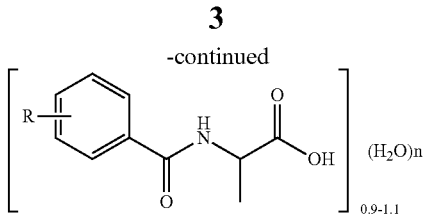

Wherein R is hydrogen, fluoro, chloro, bromo, methyl, ethyl, isopropyl, methoxy, nitro group in ortho, meta, and para positions, n is 0, ½, and 1 and a method for producing such complexes. In addition, the phenyl group can also be di- and tri-substituted with R groups. Valine and alanine in N-benzoyl-alanine can be in D and L forms.

More specifically, the present invention relates to L-valine: N-benzoyl-L-alanine complex and its use as intermediate for the optical resolution of DL-valine and for the purification of crude L-valine. When N-benzoyl-D-alanine is used as resolving agent, D-valine is obtained in the intermediate of D-valine:N-benzoyl-D-alanine complex.

The valine to be optically resolved may be a racemic mixture of L-isomer and D-isomer or a mixture in which one isomer is present in more than half the molar amount of the mixture against its antipode. Also suitable is an aqueous solution of crude DL-valine obtained synthetically in which hydantoin is formed during the reaction.

The L-valine to be purified in the process of the present invention may be any L-valine-containing aqueous solution. Examples of L-valine-containing aqueous solutions include a mixed amino acid solution by separating and removing basic amino acids from a hydrolysate formed by hydrolyzing proteins, such as soy protein and keratin, a fermentation solution obtained by incubating microorganisms capable of accumulating L-valine, a solution obtained by removing cells from this fermentation solution.

The N-benzoyl-alanine used in the present invention can be easily and inexpensively prepared by acylation of alanine under Schotten-Baumann reaction conditions. For example, N-benzoyl-L-alanine is prepared by reaction of L-alanine with benzoyl chloride under alkaline condition, followed by acidification with an acid, e.g., sulfuric, hydrochloride, formic acid, and acetic acid. The crystalline N-benzoyl-L-alanine is separated by filtration or centrifugation.

The N-benzoyl-L-alanine may be used in the form of its free acid, or its water-soluble salt. Examples of suitable water soluble salts include alkali metal salts such as sodium salt or potassium salt, or an ammonium salt. N-benzoyl-L-alanine or its water-soluble salt is used in an amount which is equimolar to or more than the molar of L-valine contained in the aqueous solution, preferably from 0.9 to 1.1 moles per mol of L-valine. While it is possible to perform the present invention using excess N-benzoyl-L-alanine or its salt, there is no advantage in using a large excess in order to obtain high efficiency in the removal of L-valine from the aqueous solution.

It is particularly interesting to note that N-benzoyl-L-alanine does not form complex with D-valine at all. When N-benzoyl-L-alanine and excess D-valine are dissolved in water and allowed to cool to crystallize, only N-benzoyl-L-alanine crystallizes from the mixture and D-valine remains in the solution. After filtration and washing, pure N-benzoyl-L-alanine is isolated without any trace of D-valine. When excess N-benzoyl-L-alanine relative to L-valine is used in the optical resolution of DL-valine, only L-valine N-benzoyl-L-alanine complex crystallizes along with excess N-benzoyl-L-alanine. The preferential reaction of N-benzoyl-L-alanine with L-valine makes the optical resolution process extremely efficient and cost-effective.

It is found that N-benzoyl-L-alanine not only reacts selectively with L-valine, but also binds exclusively to L-valine among the amino acids tested in the present invention. Examples of amino acids that do not form a complex with N-benzoyl-L-alanine are the naturally occurring ones, i.e., alanine, leucine, isoleucine, serine, glycine, cysteine, glutamine, methionine, serine, threonine, tyrosine, proline, asparagines, aspartic acid, glutamic acid, phenylalanine, and tryptophan; the unnatural amino acids, i.e., phenylglycine, p-hydroxyphenylglycine, 2-aminobutyric acid, norvaline, norleucine, homoserine, homophenylalanine. When N-benzoyl-L-alanine is added to a solution of L-valine and other amino acid mixtures, only L-valine N-benzoyl-L-valine complex crystallizes out, while other amino acids remain in the solution. This novel finding provides an industrially advantageous process for the purification of L-valine via an intermediate of L-valine N-benzoyl-L-alanine complex.

The solvent used for the purpose of the invention is not especially limited, provided the valine complex and valine dissolves in the solvent at a temperature of between room temperature and its boiling point, and the sparingly soluble complex separates out by cooling or concentrating the solution or by adding another solvent to the solution. Suitable solvents are water, hydrophilic organic solvents (e.g., methanol, ethanol, isopropanol, acetone, acetic acid, and N,N-dimethylformamide, N-methylpyrrolidinone,) and their mixtures. It is preferred that water is used as the most suitable solvent for the process of the present invention.

Although the temperature in the preparation of the solution of the complex is not particularly limited so long as it is 0° C. or above, it is desirably in the range from 45° C. to the boiling point of a solvent.

Although the temperature of crystallization is not particularly limited so long as it is below the boiling point of a solvent used, it is desirably in the range from 0° C. to 60° C.

The agitation time during crystallization is not particularly limited, and a stirring time of, for example, 30 minutes is sufficient.

Although the addition of seed crystals is not necessary for the crystallization of the optically active complex, a small amount of seed crystals may be added without any objection in order to accelerate crystallization.

Furthermore, the use of an aldehyde in crystallization is desirable because the degree of resolution can be increased markedly. The aldehydes which can be used include aromatic aldehydes and aliphatic aldehydes. Examples of them include acetaldehyde, propionaldehyde, butyraldehyde, isobutyraldehyde, glyoxal, glyoxalic acid, benzaldehyde, salicylaldehyde, p-hydroxybenzaldehyde, anisaldehyde, and vanillin. These aldehydes are used preferably in an amount of 0.01 to 2 times, by mole, preferably 0.02 to 0.1 times, by mole, of DL-valine.

Although the stirring time for crystallization in the presence of an aldehyde is not particularly limited, a longer time, for example, 3 hours to 48 hours, is desirable for the purpose of increasing the yields of the sparingly soluble complex.

It is preferred that the concentration of the L-valine N-benzoyl-L-alanine complex in a solvent is 10 to 60%, desirably 25-45% w/v. However, practical concentration of the formed complex is limited by the solubility of D-valine left in the solution after the precipitation of L-valine. It is known that D-valine is only soluble to about 8-10% at room temperature. If the concentration of the remaining D-valine exceeds the limit of its solubility, D-valine will crystallize from aqueous solution and thus lower the optical purity of L-valine.

To further increase the productivity, it is found that the L-valine N-benzoyl-L-alanine complex can be formed in an aqueous solvent containing an acidic compound having a pKa value of 0.90 to 2.10; that the amount of a mother liquor of optical resolution and purification can be decreased to ½ to ⅕ of that when no acidic compound is used.

Examples of the acidic compounds used in this invention include hydrochloric acid, hydrobromic acid, sulfuric acid, sulfurous acid, bisulfates, phosphoric acid, phosphorous acid, sulfamic acid, organic sulfonic acid, among which sulfuric acid, bisulfates, and hydrochloric acid are desirable.

The amount of the acidic compound used is such that the molar equivalent is more or less the same as that of D-valine and other amino acids. The acidic compound will form an acidic salt of D-valine and other amino acids, which are more soluble than their neutral species.

The precipitated L-valine N-benzoyl-L-alanine crystals may be separated by conventional solid-liquid separation methods such as filtration or centrifugation. Although the separated crystals have high purity, they can be further purified by a conventional purification method such as washing, dehydration, or recrystallization.

The thus obtained crystalline L-valine N-benzoyl-L-alanine complex comprising 1 mol of L-valine and 1 mol of N-benzoyl-L-alanine is a novel product which exhibits the following properties:
  White needle crystals.
  Slightly soluble in methanol; insoluble in ethanol, acetone, chloroform, and toluene.
  Solubility in water: 1.6% by weight (25° C.)
  Elemental analysis: found: C, 58.0%; H, 7.1%; N, 9.1%; Calculated: C, 58.05%; H, 7.15%; N, 9.03%.

Optically active L-valine of high purity is obtainable by hydrolyzing the optically active L-valine N-benzoyl-L-alanine complex with either an acid or a base according to methods known in prior arts. For example, the isolation can be readily performed by acidifying an aqueous suspension of the complex to precipitate N-benzoyl-L-alanine and passing the acidic solution through a weak anion exchange column to yield an aqueous solution of L-valine. After evaporation, crystalline L-valine is obtained.

As has been described, the novel substances of the present invention are useful as intermediates for the optical resolution of DL-valine and for the purification of L-valine. The process according to the present invention has the following advantages compared to the known methods:
1. It is not necessary to convert the valine to be resolved into a derivative;
2. The optically active resolving agent or selective precipitating agent is stable, inexpensive, and easy to recover in high yield for its reuse;
3. The yield and purity of the final product obtained in the process are exceedingly high for an industrially applicable process;
4. Water is used as the most suitable solvent in the process.

The present invention is further illustrated in the following examples, which are not intended in any way to limit the scope of the invention. One skilled in the art can easily modify the details to suit the inputs and desired outcomes without affecting the present invention.

EXAMPLES

Chemical and enantiomeric purity of the L-valine, D-valine, and their N-benzoyl-L-alanine complexes are determined by using chiral HPLC method under the following conditions:

Column: Crownpak CR(+), 150×4 mm.
Mobile phase: pH 1.3 $HClO_4$; Flow rate: 1.0 mL/min.
Column temperature: 25° C.
Detector: Agilent 1100 (UV detector, 200 nm).

Example 1

Twenty four grams of DL-valine and 19.3 g of N-benzoyl-L-alanine were suspended in 200 mL of deionized water. The suspension was heated to 95° C. to form a clear solution, which was cooled slowly. When the solution was cooled to room temperature after 2 hours, the precipitated crystals were separated by filtration, washed with 50 mL of deionized water, and dried to obtain 26.8 g of crystalline L-valine N-benzoyl-L-alanine complex (L-valine to N-benzoyl-L-alanine molar ratio of 1:1).

Chiral HPLC analysis of the crystal showed a purity of 99.9% L-valine.

The mother liquor was passed through a column filled with Dowex M43 weak anion exchange resin. D-valine fractions were combined and evaporated to crystalline suspension.

After filtration and drying, 9.1 g of D-valine was obtained.

Chiral HPLC assay showed a purity of 99.8% D-valine, 0.2% L-valine.

Specific rotation $[\alpha]_D^{20}=-27.6°$ (c=8, 6N HCl).

The crystalline complex was suspended in 100 mL of deionized water, to which was added 6 g of sulfuric acid. After being stirred for 1 hour, the precipitated N-benzoyl-L-alanine was filtered off and washed with 20 mL of deionized water. The filtrate was then passed through a column filled with Dowex M43 resin and the L-valine fractions were combined and evaporated to dry to obtain 9.9 g of L-valine.

Chiral HPLC assay showed a purity of 99.9% L-valine.

Specific rotation $[\alpha]_D^{20}=+28.1°$ (c=8, 6N HCl).

Example 2

Twenty-four grams of DL-valine and 38.6 g of N-benzoyl-L-alanine are suspended in 200 mL of deionized water. A clear solution was obtained by warming up to 95° C. After stirring and cooling to 22° C. in 2 hours, the crystalline suspension is filtered and the solid is washed with 50 mL of deionized water. The solid was dried and the assay found it to contain 10.4 g of L-valine and 34.8 g of N-benzoyl-L-alanine.

Chiral HPLC assay showed a purity of 99.9% L-valine.

Example 3

Forty-eight grams of DL-valine and 38.6 g of N-benzoyl-L-alanine are dissolved in 200 mL of deionized water containing 19.8 g of 98% sulfuric acid by warming up to 95° C. After cooling slowly to 22° C. in 2 hours, the crystalline precipitate is filtered, washed with 40 mL of deionized water, and dried to obtain 56.8 g of L-valine N-benzoyl-L-alanine complex.

Chiral HPLC assay showed a purity of 99.9% L-valine in the complex.

Example 4

Forty-eight grams of DL-valine and 38.6 g of N-benzoyl-L-alanine are dissolved in 200 mL of deionized water containing 20.0 g of 30% hydrochloric acid by warming up to 90° C. The solution was cooled slowly to 20° C. in 2 hours while stirring. The resulting crystalline precipitate is filtered, washed with 40 mL of deionized water, and dried to obtain 58.8 g of L-valine N-benzoyl-L-alanine complex.

Chiral HPLC assay revealed a purity of 99.9% L-valine in the complex.

Example 5

Twelve grams of L-valine, 5.0 g of L-leucine, 5.0 g of L-isoleucine, 3.0 g of L-alanine, 3.0 g of L-serine, 3.0 g of L-threonine, 3.0 g of L-phenylalanine, and 3.0 g of L-methionine were dissolved in 200 mL of deionized water, to which was added 19.8 g of N-benzoyl-L-alanine. The suspension was warmed to 85° C. to obtain a clear solution, which was slowly cooled to 22° C. while stirring. The resulting crystalline precipitate is filtered, washed with 50 mL of deionized water, and dried to obtain 26.8 g of solid.

Chiral HPLC analysis revealed the solid is L-valine N-benzoyl-L-alanine complex and the content of L-valine was 99.7%, L-alanine 0.3%. Other amino acids, present in the solution, were not detected in the solid.

Example 6

Twenty-four grams of DL-valine and 19.3 g of N-benzoyl-D-alanine were dissolved in 200 mL of deionized by heating to 95° C. The clear solution is cooled to 22° C. in 2 hours. The resulting crystalline precipitate is filtered, washed with 40 mL of deionized water, dried to obtain 28.7 g of D-valine N-benzoyl-D-alanine complex (the molar ratio was found to be 1:1).

Chiral HPLC assay revealed a purity of 99.8% D-valine in the complex.

Example 7

Twelve grams of D-valine and 19.6 g of N-benzoyl-L-alanine were dissolved in 200 mL of deionized water by heating to 88° C. The clear solution is cooled to 22° C. in 2 hours while stirring. The crystalline precipitate is filtered, washed with 40 mL of deionized water, and dried to obtain 17.5 g of solid.

Analysis showed that the crystalline solid is the recovered N-benzoyl-L-alanine. No D-alanine was found in the solid.

Example 8

Twenty-four grams of DL-valine and 23.5 g of N-(p-chlorobenzoyl)-L-alanine were dissolved in 250 mL of deionized by heating to 95° C. The clear solution is cooled to 22° C. in 2 hours. The resulting crystalline precipitate is filtrated, washed with 40 mL of deionized water, dried to obtain 28.7 g of L-valine N-(p-chlorobenzoyl)-L-alanine complex (the molar ratio was found to be 1:1).

Chiral HPLC assay revealed a purity of 99.9% L-valine in the complex.

Example 9

Twenty-four grams of DL-valine and 21.3 g of N-(p-fluorobenzoyl)-L-alanine were dissolved in 250 mL of deionized by heating to 85° C. The clear solution is cooled to 22° C. in 2 hours. The resulting crystalline precipitate is filtrated, washed with 40 mL of deionized water, dried to obtain 26.3 g of L-valine N-(p-fluorobenzoyl)-L-alanine complex (the molar ratio was found to be 1:1).

Chiral HPLC assay revealed a purity of 99.5% L-valine in the complex.

Example 10

Twenty four grams of DL-valine and 19.3 g of N-benzoyl-L-alanine were suspended in 200 mL of deionized water. The suspension was heated to 95° C. to form a clear solution, to which 0.2 g of salicylaldehyde was added. The solution was cooled slowly to room temperature and stirred for another 48 hours at 25° C. The precipitated crystals were then separated by filtration, washed with 50 mL of deionized water, and dried to obtain 29.2 g of crystalline L-valine N-benzoyl-L-alanine complex (L-valine to N-benzoyl-L-alanine molar ratio of 1:1).

Chiral HPLC analysis of the crystal showed a purity of 99.9% L-valine.

What is claimed is:

1. A method for preparing an optically active L-valine N-benzoyl-L-alanine complex and an optically active D-valine N-benzoyl-D-alanine complex by reacting valine and N-benzoyl alanine, wherein the complexes are of the general formula:

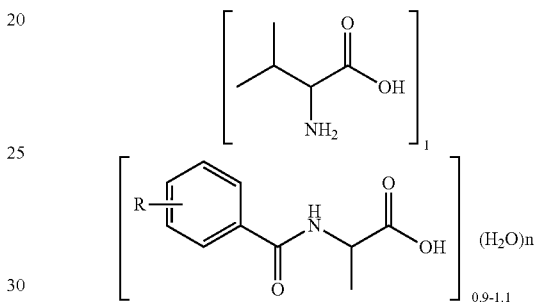

in which R is hydrogen, fluoro, chloro, bromo, methyl, ethyl, isopropyl, methoxy, nitro group in ortho, meta, and para positions, n is 0, ½, and the phenyl group can also be di- and tri-substituted with R groups, and in which alanine is L-alanine and D-alanine.

2. The method according to claim 1, wherein the optical resolution of DL-valine comprises of: (1) reacting DL-valine with an optically active N-benzoyl-L-alanine in a solvent or a solvent mixture; (2) separating the resulting crystalline L-valine N-benzoyl-L-alanine complex; (3) dissociating the L-valine N-benzoyl-L-alanine complex with either an acid or a base to obtain L-valine.

3. The method according to claim 2, wherein N-benzoyl-D-alanine is used to obtain D-valine N-benzoyl-D-alanine complex.

4. The method according to claim 2, wherein the molar ratio of optically active N-benzoyl-alanine to DL-valine is from 0.4:1 to 4:1.

5. The method according to claim 2, wherein an acidic compound is introduced into the solution to increase the solubility of undesired isomer and thus to decrease the volume of resolution solution.

6. The method according to claim 2, wherein an aldehyde is added to resolution solution to increase the yield for the formation of optically active valine N-benzoyl-alanine complex.

7. The method according to claim 1, wherein the purification of crude L-valine comprises of reacting N-benzoyl-L-alanine selectively with L-valine to form L-valine N-benzoyl-L-alanine complex as an intermediate in the presence of alanine, leucine, isoleucine, threonine, serine, cysteine, cystine, aspartic acid, glutamic acid, phenylalanine, and tyrosine.

8. The method according to claim 7, wherein an acidic compound is added to a solution of the mixture of amino acids to form acidic salts of amino acids other than L-valine.

9. The method according to claim 7, wherein said crude L-valine is obtained from hydrolysis of a protein.

10. The method according to claim 7, wherein said crude-L-valine is obtained by fermenting a microorganism that produces and accumulates L-valine and removing cells of said microorganism.

* * * * *